United States Patent [19]

Tobiki et al.

[11] 4,003,887
[45] Jan. 18, 1977

[54] NOVEL PENICILLINS AND THEIR PREPARATION

[75] Inventors: Hisao Tobiki, Toyonaka; Hirotada Yamada; Iwao Nakatsuka, both of Nishinomiya; Kozo Shimago, Takarazuka; Shigeru Okano, Kawanishi; Takenari Nakagome, Nishinomiya; Toshiaki Komatsu, Takarazuka; Akio Izawa, Toyonaka; Hiroshi Noguchi, Takarazuka; Yasuko Eda, Toyonaka, all of Japan

[73] Assignee: Sumitomo Chemical Company, Limited, Japan

[22] Filed: Sept. 3, 1975

[21] Appl. No.: 609,982

Related U.S. Application Data

[62] Division of Ser. No. 424,271, Dec. 13, 1973, Pat. No. 3,954,753.

[30] Foreign Application Priority Data

Dec. 15, 1972 Japan .............. 47-126634

[52] U.S. Cl. ..................... 260/239.1; 424/271
[51] Int. Cl.² ......................... C07D 499/68
[58] Field of Search .................. 260/239.1

[56] References Cited

UNITED STATES PATENTS

| | | | |
|---|---|---|---|
| 3,192,198 | 6/1965 | Naylor et al. | 260/239.1 |
| 3,433,784 | 3/1969 | Long et al. | 260/239.1 |
| 3,579,501 | 5/1971 | McGregor | 260/239.1 |
| 3,835,115 | 9/1974 | Richardson | 260/239.1 |
| 3,864,329 | 2/1975 | Tobiki et al. | 260/239.1 |
| 3,870,708 | 3/1975 | Gruszecki et al. | 260/239.1 |

*Primary Examiner*—Gerald A. Schwartz
*Attorney, Agent, or Firm*—Stewart and Kolasch

[57] ABSTRACT

Novel penicillins of the formula:

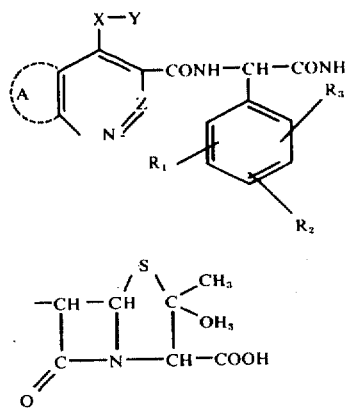

wherein the ring A is a benzene ring or a 5 or 6-membered heteroaromatic ring containing one or two nitrogen atoms as the hetero atom, on which one or more of lower alkyl, lower alkoxy, lower alkylthio, lower haloalkyl, lower alkylenedioxy halogen, hydroxyl, nitro, free or protected amino, lower alkylamino, di(lower)alkylamino and lower alkanoylamino may be present, Z is a nitrogen atom or a methylene group, X is an oxygen atom or a sulfur atom, Y is a hydrogen atom, a lower alkoxycarbonyl group or a lower alkanoyl group, $R_1$ is a free or protected hydroxyl group and $R_2$ and $R_3$ are each a hydrogen atom or a halogen atom, and their non-toxic pharmaceutically acceptable salts, and their preparation.

13 Claims, No Drawings

NOVEL PENICILLINS AND THEIR PREPARATION

This application is a division of copending application Ser. No. 424,271, filed on Dec. 13, 1973 now U.S. Pat. No. 3,954,753.

The present invention relates to novel penicillins and their preparation. More particularly, it relates to novel penicillins and their non-toxic, pharmaceutically acceptable salts, which are useful as antimicrobial agents having a broad antimicrobial spectrum including Pseudomonas, and to their preparation.

It is well known that 6-(α-aminoacylamido)penicillanic acid derivatives such as 6-(α-aminophenylacetamido)penicillanic acid (Ampicillin), 6-(α-amino-p-hydroxyphenylacetamido)penicillanic acid (Amoxycillin), 6-(α-amino-thienylacetamido)penicillanic acid, 6-(1-amino-cyclohexane)carboxamidopenicillanic acid (Cyclacillin), 6-(α-amino-isothiazolylacetamido)penicillanic acid and 6-[α-amino-2-(1,4-hexadienylacetamido)]penicillanic acid (Epicillin) inhibit the growth of various gram-positive and gram-negative bacteria. Particularly, ampicillin is one of the excellent chemotherapeutics. These compounds, however, do not exert any appreciable antimicrobial activity against Pseudomonas. In U.S. Pat. No. 3,433,784, there are described some N-acyl derivatives of ampicillin as showing a minimal inhibitory concentration of 125 to 250 μg/ml against Pseudomonas pyocinea A or R 59, when determined by the standard test method. The anit-Pseudomonas activity of the compounds as described in the working examples is, however, not so high and the antimicrobial activity against other gram-positive and gram-negative bacteria is considerably low. Thus, it may be said that the N-acyl derivatives of ampicillin are less valuable than ampicillin itself from the practical viewpoint.

As the result of the study seeking novel penicillins which have a broad antimicrobial spectrum and are highly active against gram-positive and gram-negative bacteria including Pseudomonas, it has been found that, among various compounds, the penicillins of the following formula characteristically exhibit a noticeable antimicrobial activity against Pseudomonas and a broad antimicrobial spectrum:

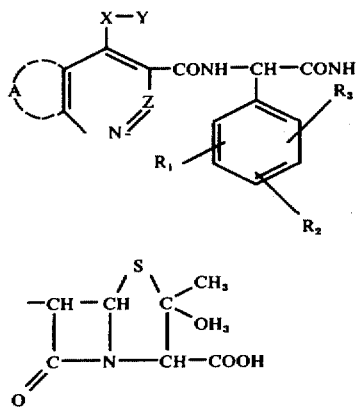

wherein the ring A is a benzene ring or a 5 or 6-membered heteroaromatic ring containing one or two nitrogen atoms as the hetero atom, on which one or more of lower alkyl, lower alkoxy, lower alkylthio, lower haloalkyl, lower alkylenedioxy, halogen, hydroxyl, nitro, free or protected amino, lower alkylamino, di(lower)alkylamino and lower alkanoylamino may be present, Z is a nitrogen atom or a methylene group, X is an oxygen atom or a sulfur atom, Y is a hydrogen atom, a lower alkoxycarbonyl group or a lower alkanoyl group, $R_1$ is a free or protected hydroxyl group and $R_2$ and $R_3$ are each a hydrogen atom or a halogen atom.

Accordingly, a main object of the present invention is to provide novel penicillins (I) and their non-toxic salts, which are useful as antimicrobial agents. Another object of this invention is to provide a process for preparing the penicillins (I) and their non-toxic salts. A further object of the invention is to provide a use of the penicillins (I) and their non-toxic salts as antimicrobial agents. These and other objects of the invention will be apparent to those conversant with the art from the foregoing and subsequent descriptions.

As to the significances of the symbols in the said formula (I) and in any other formula as hereinafter shown, the term "lower alkyl" is intended to mean generally both straight and branched chain aliphatic hydrocarbon groups having not more than eight carbon atoms (preferably not more than five carbon atoms) such as methyl, ethyl, propyl, isopropyl, butyl, isobutyl, amyl and isoamyl. Similarly where the term "lower" is used as a part of the description of any other group (e.g. lower alkoxy, lower alkylthio, lower haloalkyl, lower alkylamino, di(lower)alkylamino), it refers to the alkyl portion of such group. Thus, the terms "lower alkanoyl" and "lower alkoxycarbonyl" means respectively alkanoyl and alkoxycarbonyl having not more than nine carbon atoms (preferably not more than six carbon atoms). Exceptionally, however, the term "lower alkylenedioxy" indicates alkylenedioxy having not more than three carbon atoms. The halogen atom includes the chlorine atom, bromine atom, iodine atom and fluorine atom.

The protected amino group and the protected hydroxyl group indicate respectively an amino group and a hydroxyl group which are protected by any protective group conventionally employed for the protection of amino or hydroxyl. Examples of the protected amino group include lower alkanoylamino and lower alkoxycarbonylamino. Examples of the protected hydroxyl group include lower alkanoyloxy and lower alkoxycarbonyloxy.

The 5 or 6-membered heteroaromatic ring containing one or two nitrogen atoms may be, for example, a pyrazole ring, a thiazole ring, an imidazole ring, a pyridine ring, a pyrazine ring, a pyridazine ring, a pyrimidine ring, etc. Among them, preferred are a pyrazole ring, a thiazole ring, a pyrazine ring and a pyrimidine ring, particularly a pyridine ring.

The non-toxic, pharmaceutically acceptable salts of the penicillins (I) are, for instance, the alkali metal salts (e.g. sodium, potassium salts), the alkaline earth metal salts (e.g. calcium, magnesium salts), the arginine salt, the substituted and unsubstituted ammonium salts, etc. Examples of the substituted ammonium salts include the salts of triethylamine, procaine, dibenzylamine, N-benzyl-β-phenethylamine, 1-ephenamine, N,N'-dibenzylethylenediamine, dehydroabiethylamine, N,N'-bis-dehydroabiethylethylenediamine, etc.

One of the structural characteristics of the penicillins (I) of the invention is that the residue

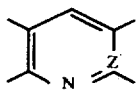

bears thereon the substituent —X—Y linked to a carbon atom adjacent to the carbon atom to which a 6-(α-aminoacylamido)penicillanic acid moiety is linked. The compounds wherein the residue

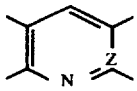

bears no such substituent are antimicrobially much less active than those bearing the substituent and exhibit only the same low antimicrobial activity as those disclosed in U.S. Pat. No. 3,433,784 against Pseudomonas as well as other gram-positive and gram-negative bacteria.

Another structural characteristic of the penicillins (I) is the presence of the substituent $R_1$. The serum and urinary concentrations in mice and rats of the compounds wherein the phenyl group bears the substituent $R_1$ are higher than those of the compounds not having such substituent.

According to the present invention, the penicillin (I) can be produced by reacting a carboxylic acid of the formula:

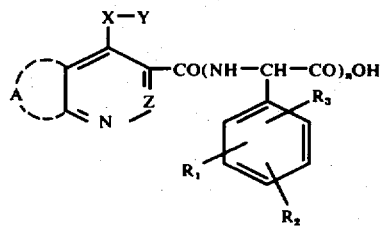

wherein A, Z, X, Y, $R_1$, $R_2$ and $R_3$ are each as defined above and n is 0 or 1, or its reactive derivative with an amine of the formula:

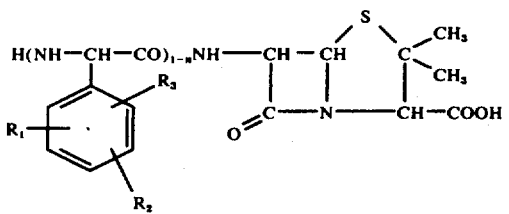

wherein $R_1$, $R_2$, $R_3$ and n are each as defined above, or its derivative, if necessary, followed by hydrolysis, reduction or acylation of the resulting product and/or elimination of any protective group.

The reaction can be carried out in a conventional coupling method and/or by the use of a conventional coupling reagent in the related art field, i.e. in the synthesis of peptides, penicillins, cephalosphorins and the like.

The compound (II) may be used as such, i.e. in a free or salt form, or as the reactive derivative. Examples of salts of the compound (II) are the salts of alkali metals, alkaline earth metals, ammonia and organic bases (e.g. trimethylamine, triethylamine, dicyclohexylamine).

The reactive derivatives of the compound (II) on the carboxyl group include, e.g. acid halides, acid anhydrides, active amides, acid azides and active esters. Among the acid halides, the use of an acid chloride is the most favorable. Examples of the acid anhydrides are mixed acid anhydrides and symmetric acid anhydrides prepared by the use of acids such as toluenesulfonic acid, an alkylcarbonic acid and an aliphatic carboxylic acid (e.g. pivalic acid). Examples of the active amides are those obtained by using imidazole, dimethylpyrazole, triazole, tetrazole or the like. Examples of the active esters are those prepared by using p-nitrophenol, pentachlorophenol, p-nitrothiophenol, N,N'-dimethylhydroxylamine, 1-hydroxy-2(1H)-pyridone, N-hydroxysuccinimide or N-hydroxyphthalimide.

When the compound (II) wherein Y is hydrogen or its reactive derivative is used, the hydroxyl group may be protected with any protective group as is conventionally employed in the related art field.

Illustrating some of the reactive derivatives of the compound (II) wherein n is 0 in detail, the mixed acid anhydride of the formula:

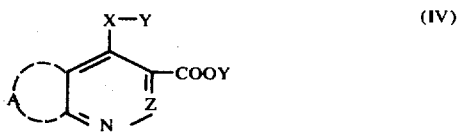

wherein A, Z and X are each as defined above and Y represents acyl or alkoxycarbonyl can be prepared by the reaction of the compound (II) wherein Y is hydrogen and n is 0 with an acyl halide or an alkyl halocarbonate. Thus, the reaction of 1 molar amount of the compound (II) with a 2 molar amount of an acyl halide (e.g. pivaloyl chloride) or an alkyl halocarbonate (e.g. ethyl chlorocarbonate, isobutyl chlorocarbonate) in the presence of a 2 molar amount of a basic substance may afford the compound (IV) in an excellent yield. (The process using the thus obtained mixed acid anhydride (IV) as the reactant will be referred to as the "mixed anhydride process".)

Another type of the reactive derivative is the compound of the formula:

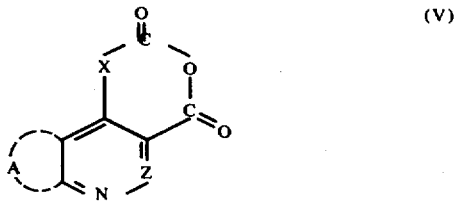

wherein A, Z and X are each as defined above, which may be prepared by the reaction of 1 molar amount of the compound (II) wherein Y is hydrogen and n is 0 with 1 molar amount of phosgene in the presence of a 2 molar amount of a basic substance. The similar type of the reactive derivative may be also prepared by the use of thionyl chloride, phosphorus trichloride or the like in place of phosgene. (The process using the above cyclic compound (V) or any similar compound thereto as the reactant will be referred to as the "phosgene process".)

Examples of the basic substance in the acid reactions are an inorganic base (e.g. sodium hydroxide, potassium hydroxide) and an organic base (e.g. triethylamine, pyridine, dimethylaniline, lutidine, N-methylmorpholine and N-methylpiperidine).

Since the reactive derivatives described above are usually very reactive and unstable to isolate, they may be used in the form of the reaction mixture for the reaction with the compound (III) wherein $n$ is 0.

The derivatives of the compound (III) may be the alkali metal salts (e.g. sodium, potassium salts), the alkaline earth metal salts (e.g. calcium, barium salts), the organic base salts (e.g. trimethylamine, triethylamine salts), the organic sulfonic acid salts (e.g. toluenesulfonic acid, naphthalenesulfonic acid, tetrahydronaphthalenesulfonic acid salts), the esters, the N-substituted derivatives, etc.

Specific examples of the derivatives of the compound (III) wherein $n$ is 0 include the following compounds:

wherein $R_1$, $R_2$ and $R_3$ are each as defined above and $R_4$, $R_5$, $R_6$, $R_7$ and $R_8$ are each a lower alkyl group.

These esters can be advantageously used in the coupling reaction, because of their higher solubility in an ordinary solvent to be used as the reaction medium and of their higher reactivity with the compound (II) than those of the corresponding free acids.

Further examples of the ester unit in the esters of the compound (III) are as follows: toluenesulfonylethyl ester, p-nitrobenzyl ester, benzyl ester, phenacyl ester, diphenylmethyl ester, substituted diphenylmethyl ester, trityl ester, benzoyloxymethyl ester, lower alkanoyloxymethyl ester, dimethylmethyleneamino ester, p-nitrophenyl ester, methylsulfonylphenyl ester, methylthiophenyl ester, t-butyl ester, 3,5-di-t-butyl-4-hydroxybenzyl ester, trichloroethyl ester etc. These ester units are all conventionally employed as a group protecting a carboxylic acid radical in the related art field.

The esters which can be prepared commercially from penicillin-G are particularly preferable. Examples of the preparation for such esters are illustratively shown in the following scheme:

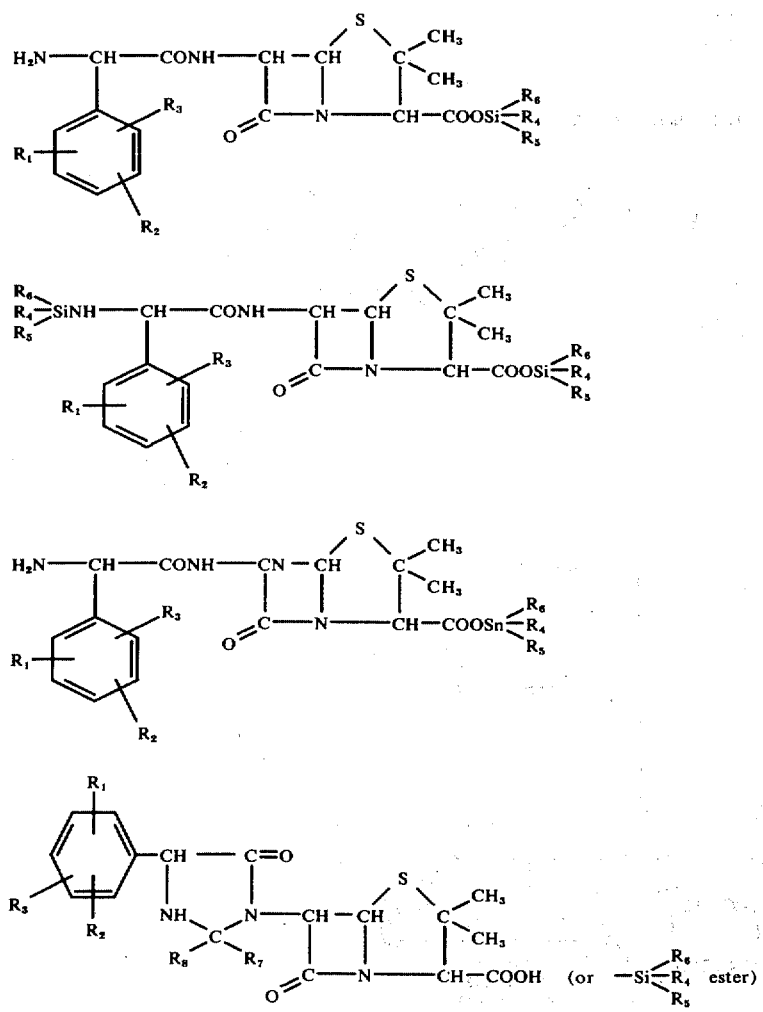

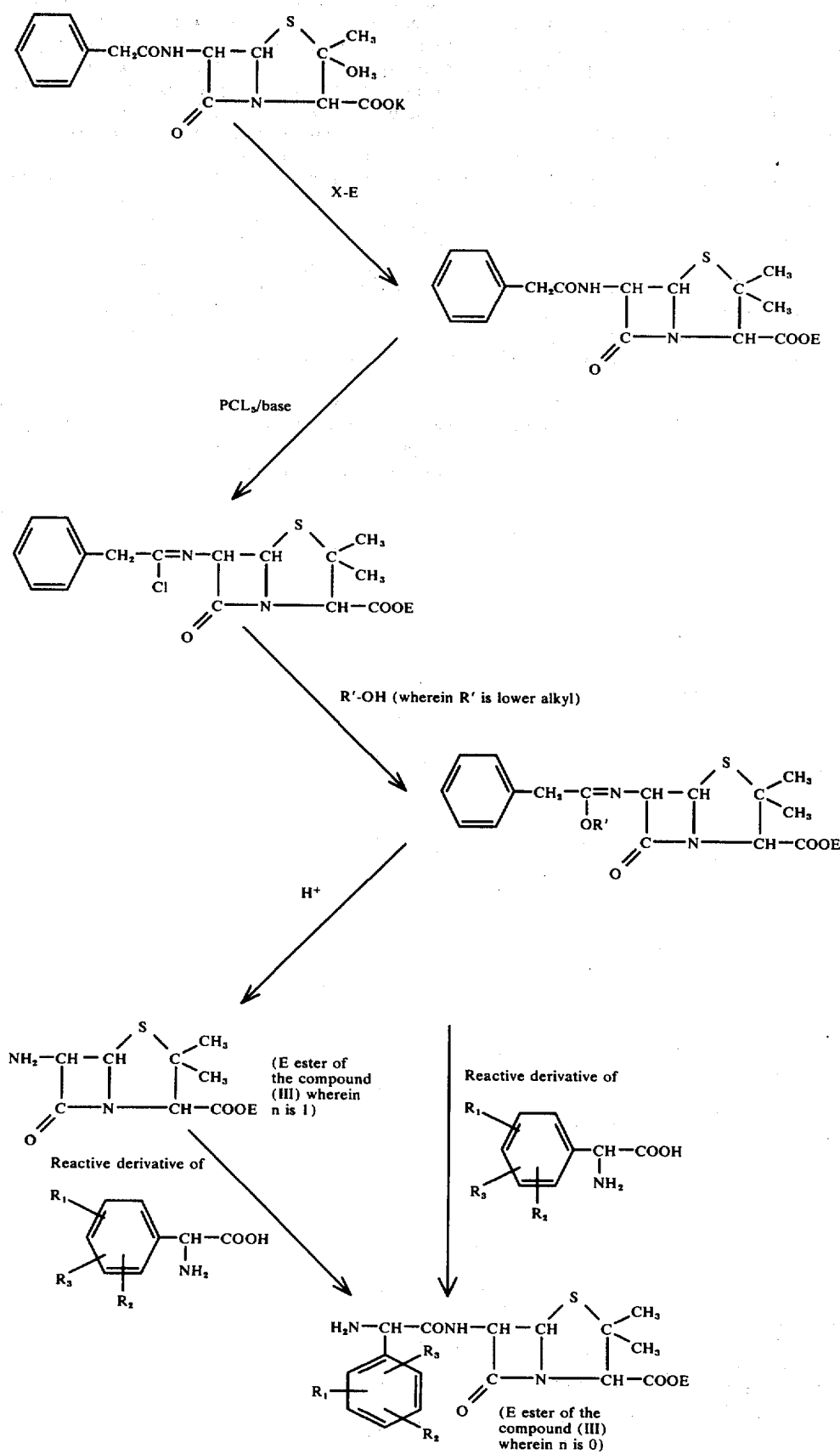

wherein $R_1$, $R_2$ and $R_3$ are each as defined above and -COOE means an ester part.

The above illustrated E ester of the compound (III) can be employed for the coupling reaction in the form of a salt with an organic or inorganic acid. Examples of the organic or inorganic acid part in such salt are toluenesulfonic acid, naphthalenesulfonic acid, tetralinesulfonic acid, hydrochloric acid, etc.

The coupling reaction of the compound (II) or its reactive derivative with the compound (III) or its derivative is usually carried out at a temperature below about 80° C, e.g. at a temperature of −50° to 80° C, but this is not limitative.

The coupling reaction is normally effected in the presence of an inert solvent. As the inert solvent, there may be used a polar solvent (e.g. dichloromethane, chloroform, acetone, tetrahydrofuran, dioxane, acetonitrile, methylisobutylketone, ethanol, dimethylformamide) or a non-polar solvent (e.g. benzene, toluene, petroleum ether, n-hexane). Water or a water-containing organic solvent is also utilizable depending on the type of starting materials used.

In case that the compound (II) is subjected to coupling in a free form or a salt form, the reaction may be carried out preferably in the presence of a conventional coupling reagent (e.g. N,N'-dicyclohexylcarbodiimide, diphenyl phosphorous acid).

In the compound (II), the substituent —X—Y may represent either a free hydroxyl or sulfhydryl group or a protected hydroxyl or sulfhydryl group. When the compound (II) wherein the substituent —X—Y represents a protected hydroxyl or sulfhydryl group is employed in the coupling reaction, the penicillin (I) wherein Y is hydrogen may be often obtained as the result of simultaneous elimination of the protective group. When the protective group is not eliminated in the course of the coupling reaction, it may be eliminated thereafter by a conventional procedure under such a mild condition that the opening of the lactam ring in the penicillin nucleus is not caused. The elimination of the protective group can be accomplished, for instance, by treating the product in the coupling reaction with an inorganic or organic basic substance (e.g. sodium carbonate, potassium carbonate, sodium hydroxide, aqueous ammonia solution, triethylamine, methylamine, dimethylamine, diethylamine, morpholine, piperidine, potassium acetate, sodium acetate, potassium 2-ethylhexanoate). In such treatment, the penicillin (I) wherein Y is hydrogen can be obtained even in an acidic condition, but the protective group is more smoothly eliminated by treatment under a basic condition.

In case that the compound (II) wherein $n$ is 0 and Y is lower alkoxycarbonyl or lower alkanoyl and the compound (III) wherein $n$ is O and $R_1$ is hydroxyl are subjected to coupling, there may be sometimes obtained the penicillin (I) wherein Y is hydrogen and $R_1$ is lower alkoxycarbonyl or lower alkanoyl. Further, the coupling reaction of the compound (III) wherein $n$ is O and $R_1$ is protected hydroxyl (e.g. ethoxycarbonyloxy, benzyloxycarbonyloxy) with the compound (II) wherein $n$ is O and Y is lower alkoxycarbonyl or lower alkanoyl may afford the penicillin (I) wherein Y is lower alkoxycarbonyl or lower alkanoyl and $R_1$ is protected hydroxyl.

When the compound (II) wherein Y is hydrogen is subjected to coupling, it may be favorably employed, for instance, in the form of the reactive ester or the acid halide on the carboxyl group whereby the penicilline (I) wherein Y is hydrogen is obtainable as the product.

The penicillin (I) wherein the ring A is substituted with an amino group may be produced from the corresponding penicillin (I) wherein the ring A is substituted with a nitro group or a protected amino group. For example, the reduction of the penicillin (I) wherein the ring A bears a nitro group or a benzyloxycarbonylamino group under such a mild condition that the opening of the lactam ring in the pencillin nucleus is not caused gives the penicillin (I) wherein the ring A bears an amino group. Further, for example, the hydrolysis of the penicillin (I) wherein the ring A bears a protected amino group (e.g. enamine) under a mild condition as above results in the elimination of the protective group to give the penicillin (I) wherein the ring a bears an amino group.

Alternatively, the penicillin (I) having an amino group on the ring a may be produced by the said coupling reaction wherein the compound (II) is used in the form of the acid halide on the carboxyl group.

When any protective group is present in the product of the coupling reaction, it may be eliminated by a per se conventional procedure such as catalytic reduction or hydrolysis, favorably under a mild condition.

The production of the penicillin (I) may be identified by thin layer chromatography, iodometry, infrared absorption spectrum and so on. The characteristic infrared absorption due to the lactam ring is at 1750 − 1800 cm$^{-1}$. A particularly effective identifying method is NMR analysis, since the signals attributed to the proton Ha of the amide bond in the following structure for the penicillin (I) appear in a very low-field, which is due to the presence of the substituent —X—Y:

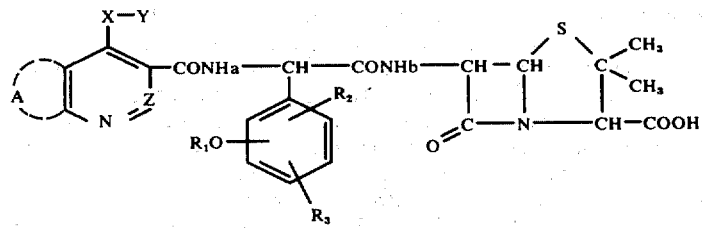

When measured in hexadeuterodimethylsulfoxide at 60 MHz using an NMR-spectral instrument, Ha and Hb signals in case of Y being a lower alkanoyl group or a lower alkoxycarbonyl group appear respectively at 540 − 570 Hz and at 630 − 680 Hz. In case of Y being a hydrogen atom, Ha and Hb signals appear respectively at 650 − 690 Hz and at 540 − 570 Hz. Ha and Hb signals in case of Y being a hydrogen atom appear in a lower field than those of Y being a lower alkanoyl group or a lower alkoxycarbonyl group.

The produced penicillin (I) may be, if desired, converted into its non-toxic pharmaceutically acceptable salt in a per se conventional manner.

Still, the compound (II) wherein n is 1 can be prepared easily by a conventional procedure, for instance, by reacting the reactive derivative of the compound (II) wherein n is O with an amino acid of the formula:

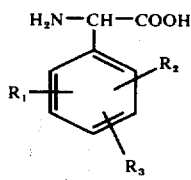

wherein $R_1$, $R_2$ and $R_3$ are each as defined above, or its ester in water or an organic solvent in the presence of a basic substance.

The amino acid may be any of the DL-, D- and L-configurations. The esters may be, for example, trialkylsilyl ester, lower alkyl ester, p-nitrophenyl ester, benzyl ester, phenylthiophenyl ester, N-hydroxysuccinimide ester, etc. These esters may be derived from the corresponding acid chlorides or prepared by any other conventional method. As the organic solvent, a polar or non-polar organic solvent (e.g. dioxane, tetrahydrofuran, dichloromethane, benzene, dimethylformamide, dimethylsulfoxide) is utilizable. Examples of the basic substance are sodium hydroxide, potassium hydroxide, triethylamine, N-methylmorpholine, dimethylaniline, etc.

When the ester is employed in the above reaction, the protective group of the resulting N-acylamino acid ester may be eliminated by a conventional procedure to give the compound (II) wherein n 1. When desired, the obtained active ester salt of the compound (II) wherein n 1 may be employed in the coupling reaction with the compound (III) wherein n is 1 to produce the penicillin (I).

The present invention is illustrated more precisely by the following Examples but those are not intended to limit the scope of the present invention.

EXAMPLE 1

Preparation of D-α-(4-hydroxy-1,5-naphthyridine-3-carboxyamido)-p-hydroxybenzylpenicillin:-

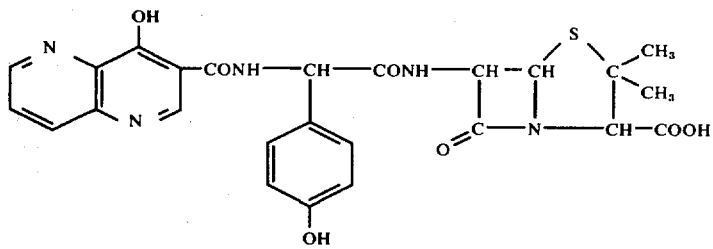

One hundred ml of dichloromethane and 2.2 g of triethylamine were added to 3.87 g of D-α-amino-p-hydroxybenzylpenicillin sodium salt, and 2.2 g of trimethylchlorosilane were dropwise added thereto. To the resulting dichloromethane solution of the pencillin trimethylsilyl ester, there were added 2.2 g of triethylamine and then 2.45 g of powdered 4-hydroxy-1,5-naphthyridine-3-carbonyl chloride hydrochloride at 0° to 5° C. The resultant mixture was stirred at 0° 5° C overnight. The reaction mixture was adjusted to pH 2 with a 11.2% solution of hydrogen chloride in dioxane while cooling with ice. The solvent was evaporated under reduced pressure, and 100 ml of ice water were added to the residue. The precipitated crystals were collected by filtration, washed with water and dissolved in an aqueous solution of sodium bicarbonate. The insoluble materials were separated by filtration, and the filtrate was adjusted to pH 2 with N hydrochloric acid while cooling with ice. The precipitated crystals were collected by filtration and dried under reduced pressure to give 3.1 g of the objective compound as crystals. Purity (determined by iodometry), 86.5%.

4-Hydroxy-1,5-naphthyridine-3-carbonyl chloride hydrochloride used as the starting material in the above Example was prepared as follows:

4-Hydroxy-1,5-naphthyridine-3-carboxylic acid was added to a mixture of benzene, 0.73 g of dimethylformamide and 1.56 g of thionyl chloride, and the resulting mixture was stirred at 40° to 85° C for 3 hours. The precipitated crystals were collected by filtration, washed with benzene and dried under reduced pressure to give 2.37 g of 4-hydroxy-1,5-naphthyridine-3-carbonyl chloride hydrochloride as crystals. Purity (determined by NMR analysis as the ester form obtained by further alcoholysis), 96.3%.

EXAMPLE 2

Preparation of DL-α-(4-hydroxy-1,5-naphthyridine-3-carboxamido)-p-hydroxybenzylpenicillin:-

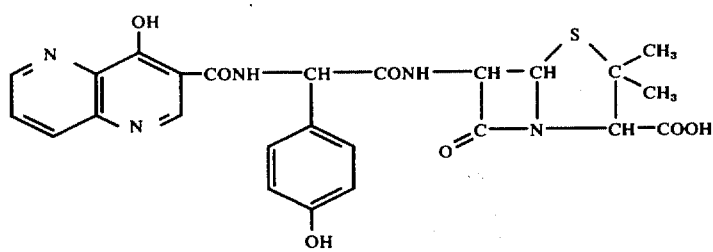

a. To the mixture of 2.22 g of DL-α-amino-p-hydroxybenzylpenicillin triethylamine salt and 15 ml of dimethylformamide, there were added 1.3 g of triethylamine and then 1.08 g of powdered 4-hydroxyl-1,5-naphthyridine-3-carbonyl chloride hydrochloride while cooling with ice, and the resulting mixture was stirred for 4 hours. The precipitate was collected by filtration, washed with dimethylformamide and dichloromethane in order to give 1.2 g of DL-α-(4-hydroxy-1,5-naphthyridine-3-carboxamido)-p-hydroxybenzylpenicillin triethylamine salt as brown crystals. IR $\nu_{C=O}$ 1775 cm$^{-1}$, 1660 cm$^{-1}$.

The filtrate and the washing solvents were combined together, and 100 ml of ether were added thereto. The insoluble material was collected by filtration and treated with 50 ml of dichloromethane. The obtained crystals were suspended in 30 ml of dichloromethane, adjusted to pH 2 with an 11.2% solution of hydrogen chloride in dioxane while cooling with ice and concentrated under reduced pressure. The residue was admixed with 30 ml of cold water, collected by filtration, washed with water and dried under reduced pressure to give 1.1 g of DL-α-(4-hydroxy-1,5-naphthyridine-3-carboxyamido)-p-hydroxybenzylpenicillin as brown crystals.

To 0.93 g of DL-α-(4-hydroxy-1,5-naphthyridine-3-carboxamido)-p-hydroxybenzylpenicillin triethylamine salt as obtained above, there were added 6 ml of dimethylformamide and then 0.792 g of 50% solution of potassium 2-ethylhexanoate in n-butanol, and the resultant mixture was stirred at room temperature for 20 minutes. After removal of insolube materials by filtration, the filtrate was added to 25 ml of acetone heated at 40 to 50° C while stirring. The precipitated crystals were immediately collected by filtration, washed with acetone and dried under reduced pressure to give DL-α-(4-hydroxy-1,5-naphthyridine-3-carboxamido)-p-phydroxybenzylpenicillin potassium salt. Purity (determined by iodometry), 87%.

In the same procedure as above, DL-α-(4-hydroxy-1,5-naphthyridine-3-carboxamido)-p-hydroxybenzylpenicillin potassium salt was prepared from DL-α-(4-hydroxy-1,5-naphthyridine-3-carboxamido)-p-hydroxybenzylpenicillin as obtained above.

b. To a suspension of 0.5 g of DL-α-(4-hydroxy-1,5-naphthyridine-3-carboxamido)-p-hydroxyphenylacetic acid in 15 ml of anhydrous dimethylsulfoxide, 0.27 g of N,N'-carbonyldiimidazole was added while stirring and cooling with ice. After 30 minutes, 0.3 g of powdered 6-aminopenicillanic acid was added thereto, and the resulting mixture was stirred for 4 hours. The reaction mixture was filtered, and the filtrate was dropwise added to 200 ml of acetone while stirring. The precipitate was collected by filtration and dried under reduced pressure. The obtained crude penicillin was dissolved in dimethylformamide and, after removal of insoluble materials by filtration, 50% solution of potassium 2-ethylhexanoate in n-butanol was added. The resultant mixture was added dropwise to 40 ml of acetone under reflux while stirring. After 10 minutes, the precipitated crystals were collected by filtration to give DL-α-(4-hydroxy-1,5-naphthyridine-3-carboxamido)-p-hydroxybenzylpenicillin potassium salt. Purity (determined by iodometry), 78%.

Dl-α-(4-Hydroxy-1,5-naphthyridine-3-carboxamido)-p-hydroxyphenylacetic acid used as the starting material in the part (b) of the above Example was prepared as follows:

To a mixture of 1.35 g of DL-2-p-hydroxyphenylglycine, 50 ml of anhydrous dichloromethane and 4.05 g of triethylamine, 2.62 g of trimethylchlorosilane were added, and the resulting mixture was refluxed for 20 minutes. After the addition of 2.1 g of 4-hydroxy-1,5-naphthyridine-3-carbonyl chloride hydrochloride, the reaction was effected while cooling with ice for 4 hours. The reaction mixture was concentrated under reduced pressure, 50 ml of water were added to the residue, and the resulting mixture was adjusted to pH 1 with 4N hydrochloric acid. The precipitated crystals were collected by filtration, suspended in 50 ml of water and potassium carbonate was added thereto. After removal of insoluble materials by filtratior, the filtrate was adjusted to pH 1. The precipitated crystals were collected by filtration, washed with water and dried to give 2.1 g of DL-α-(4-hydroxy-1,5-naphthyridine-3-carboxamido)-p-hydroxyphenylacetic acid. M.P. 310° to 320° C (decomp.).

EXAMPLE 3

Preparation of DL-α-(4-hydroxy-6-dimethylamino-1,5-naphthyridine-3-carboxamido)-p-ethoxycarbonyloxybenzylpenicillin:-

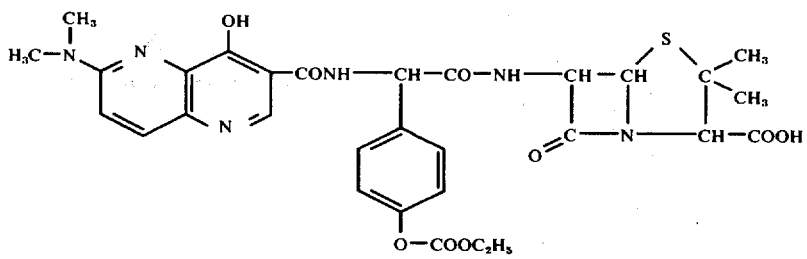

In a mixture of 80 ml of dichloromethane and 1.01 g of triethylamine, 1.17 g of 4-hydroxy-6-dimethylamino-1,5-naphthyridine-3-carboxylic acid were suspended, and 1.09 g of ethyl chlorocarbonate were added thereto at −20 to −25° C. After the reaction is effected for 1 hour, a mixture of 1.85 g of powdered DL-α-amino-p-hydroxybenzylpenicillin triethylamine salt, 30 ml of dichloromethane and 0.25 g of triethylamine was poured therein, and the resulting mixture was stirred at −25° C for 5 hours. The reaction mixture was admixed with a solution of 1.26 g of sodium bicarbonate in 300 ml of water and shaken with 300 ml of ethyl acetate.

The aqueous layer was separated and adjusted to pH 3.5 with N hydrochloric acid. The precipitated crystals were collected by filtration, washed with water and dried under reduced pressure to give 2.26 g of DL-α-(4-hydroxy-6-dimethylamino-1,5-naphthyridine-3-carboxamido)-p-ethoxycarbonyloxybenzylpenicillin.

EXAMPLE 4

Preparation of D-α-(4-hydroxyquinoline-3-carboxamido)-p-pivaloyloxybenzylpenicillin:-

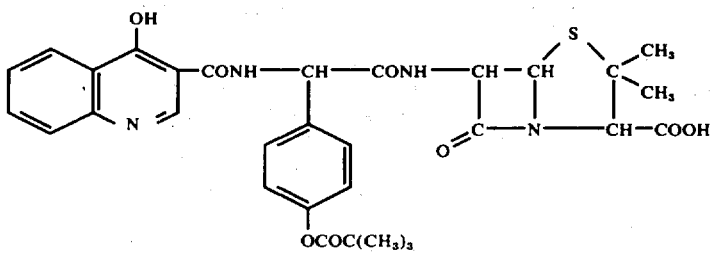

To a mixture of 1.88 g of 4-hydroxyquinoline-3-carboxylic acid, 60 ml of dichloromethane and 2.02 g of triethylamine while cooling with ice and stirring, 2.5 g of pivaloyl chloride were added dropwise for 1 hour. To the resulting mixture, 4.67 g of powdered D-α-amino-p-hydroxybenzylpenicillin triethylamine salt were added, and the reaction was effected. The reaction mixture was admixed with an 11.2% solution of hydrogen chloride in dioxane to make pH 2 and concentrated under reduced pressure. The residue was suspended in 60 ml of ice water, and the precipitate was collected by filtration and dried under reduced pressure to give D-α-(4-hydroxyquinoline-3-carboxamido)-p-pivaloyloxybenzylpenicillin as crystals. Purity (determined by iodometry), 78.3%.

EXAMPLE 5

Preparation of D-α-(4-ethoxycarbonyloxy-1,5-naphthyridine-3-carboxamido)-p-benzyloxycarbonyloxybenzylpenicillin:

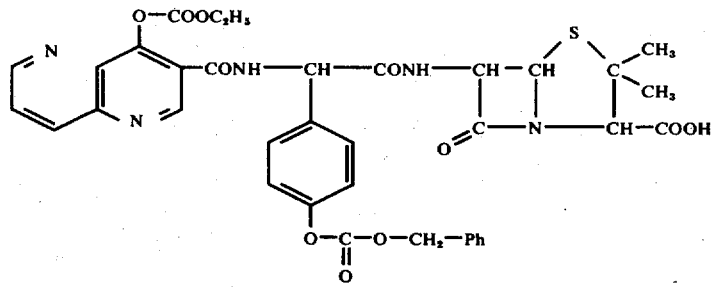

To a mixture of 0.95 g of powdered 4-hydroxy-1,5-naphthyridine, 20 ml of dichloromethane and 1.1 g of triethylamine maintained at 0° to 5° C, 0.55 g of ethyl chlorocarbonate was added, and the resultant mixture was stirred for 30 minutes. Then, 2.9 g of D-α-amino-p-benzyloxycarbonyloxybenzylpenicillin triethylamine salt were added thereto, and the reaction was effected for 7 hours. The reaction mixture was adjusted to pH 2 at 0° C with an 11.2% solution of hydrogen chloride in dioxane and concentrated under reduced pressure. The residue was admixed with 20 ml of ice water and adjusted to pH 2. The precipitated crystals were collected by filtration and washed with water to give D-α-(4-ethoxycarbonyloxy-1,5-napthyridine-3-carboxamido)-p-benzyloxycarbonyloxybenzylpenicillin. Purity (determined by iodometry, 76%.

EXAMPLE 6

Preparation of DL-α-(4-hydroxyquinoline-3-carboxamido)-p-hydroxybenzylpenicillin:

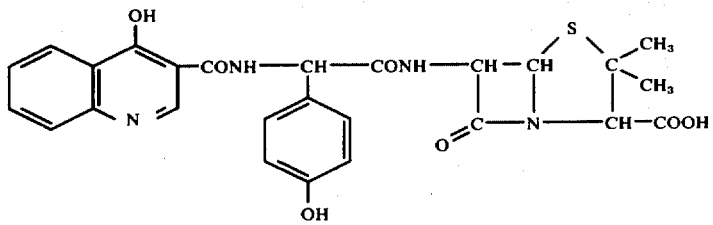

To a mixture of 1.88 g of 4-hydroxyquinoline-3-carboxylic acid, 60 ml of dichloromethane and 2.2 g of triethylamine kept at −20° to −25° C, 9.9 g of 10% solution of phosgene in dichloromethane were dropwise added, and the resultant mixture was stirred for 30 minutes. Then, 3.9 g of powdered DL-α-amino-p-hydroxybenzylpenicillin sodium salt were added thereto, and the reaction was effected at the same temperature as above for 5 hours and at 0° C for 1 hour. The reaction mixture was treated as in Example 4 to give 3.8 g of DL-α-(4-hydroxyquinoline-3-carboxamido)-p-hydroxybenzylpenicillin. Purity (determined by iodometry, 81.5%.

EXAMPLE 7

Preparation of D-α-(4-hydroxy-7-methyl-1,8-naphthyridine-3-carboxamido)-p-hydroxybenzylpenicillin:-

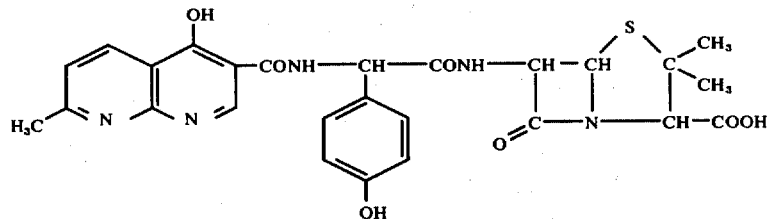

To a solution of 0.5 g of D-α-amino-p-hydroxybenzylpenicillin sodium salt in 50 ml of dimethylformamide, 0.387 g of powdered 4-hydroxy-7-methyl-1,8-naphthyridine-3-carboxylic acid p-nitrophenyl ester was added, and the resulting mixture was stirred at room temperature for 10 hours. After removal of insoluble materials be filtration, 200 ml of ether were added to the filtrate. The precipitate was collected by filtration, dissolved in 10 ml of water and adjusted to pH 2 with dilute hydrochloric acid while cooling with ice. The precipitated crystals were collected by filtration and dried under reduced pressure to give D-α-(4-hydroxy-7-methyl-1,8-naphthyridine-3-carboxamido)-p-hydroxybenzylpenicillin. Purity (determined by iodometry), 82.7%.

4-Hydroxy-7-methyl-1,8-naphthyridine-3-carboxylic acid p-nitrophenyl ester used as the starting material in the above Example was prepared as follows:

A mixture of 1 g of 4-hydroxy-7-methyl-1,8-naphthyridine-3-carboxylic acid and 25 ml of anhydrous pyridine was heated on an oil bath at 50° to 60° C while stirring. Then, 1.38 g of p-nitrophenyl trifluoroacetate were added thereto and, after the heating was interrupted, stirring was carried out for 2 hours. The precipitated crystals were collected by filtration and washed with ethanol to give 4-hydroxy-7-methyl-1,8-naphthyridine-3-carboxylic acid p-nitrophenyl ester as pale yellow crystalline powder melting at 311 to 313° C (decomp.). Yield, 1.2 g. IR $\nu_{C=O}$ 1700 cm$^{-1}$; $\nu_{NO}$ 1520 cm$^{-1}$, 1345 cm$^{-1}$.

EXAMPLE 8

Preparation of D-α-(4-hydroxycinnoline-3-carboxamido)-p-hydroxybenzylpenicillin:-

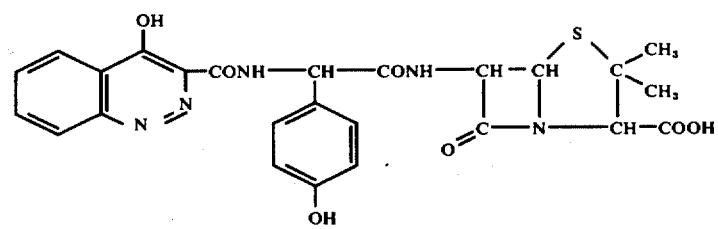

In 30 ml of anhydrous dimethylformamide, 0.95 g of 4-hydroxycinnoline-3-carboxylic acid was dissolved at room temperature, and 0.89 g of carbonyldiimidazole was added thereto. After 30 minutes, a solution of 2.34 g of D-α-amino-p-hydroxybenzylpenicillin triethylamine salt in 20 ml of dimethylformamide was added to the resulting mixture, and stirring was continued at room temperature for 6 hours. After the addition of 1.82 g of a 50 % solution of potassium 2-ethylhexanoate in n-butanol and then ether, the resultant mixture was filtered. The collected substance was dissolved in water and adjusted to pH 2 with N hydrochloric acid while cooling with ice. The precipitate was collected by the filtration and dried over phosphorus pentoxide under reduced pressure to give 1.7 g of D-α-(4-hydroxycinnoline-3-carboxamido)-p-hydroxybenzylpenicillin. This product was suspended in 50 ml of acetane, 1.4 g of 50 % solution of potassium 2-ethylhexanoate in n-butanol were added to the suspension, and refluxing was continued for 5 minutes. The precipitated crystals were collected by filtration while hot to give 1.6 g of D-α-(4-hydroxycinnoline-3-carboxamido)-p-hydroxybenzylpenicillin potassium salt. Purity (determined by iodometry), 86.2%.

EXAMPLE 9

Preparation of D-α-(4-hydroxy-1,5-naphthyridine-3-carboxamido)-p-ethoxycarbonyloxybenzylpenicillin:- utes. After the addition of 2.9 g of D-α-amino-p-hydroxybenzylpenicillin 3', 5'-di-t-butyl-4'-hydroxybenzyl ester (prepared from penicillin G according to a conventional procedure), the reaction was effected at the same temperature as above overnight. The solvent was removed from the reaction mixture by distillation under reduced pressure, and cold water was added thereto. The insoluble material was collected by filtration and dried under reduced pressure. The thus obtained product was admixed with 30 ml of anhydrous dimethylformamide and 1.8 g of potassium 2-ethylhexanoate, and the resulting mixture was dropwise added to 100 ml of acetone. The precipitate was collected by filtration and washed with acetone to give D-α-(4-hydroxy-1,5-naphthyridine-3-carboxamido)-p-ethoxycarbonyloxybenzylpenicillin potassium salt. Purity

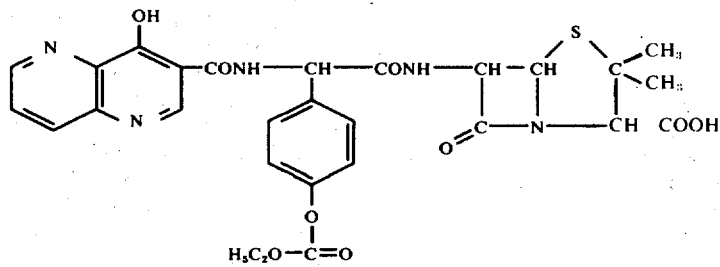

To a mixture of 0.95 g of powdered 4-hydroxy-1,5-naphthyridine-3-carboxylic acid, 25 ml of dichloromethane and 1.1 g of triethylamine, 1.1 g of ethyl chlorocarbonate were added at 0° C, and the resultant mixture was stirred at the same temperature for 40 minutes.

(determined by iodometry), 78.7%.

EXAMPLES 10–41

In the same procedure as above, there were produced the penicillins (I) as shown in Table 1.

Table 1

| Example No. | L | $R_1$ | $R_2$ | $R_3$ | M | Purity (%) |
|---|---|---|---|---|---|---|
| 10 | 7-Cl-4-OH-quinoline-3-yl | p-OCOOC$_2$H$_5$ | H | H | H | 81.3 |
| 11 | 7-CF$_3$-4-OH-quinoline-3-yl | p-OH | H | H | K | 83.0 |
| 12 | 4-OCOOC$_2$H$_5$-quinoline-3-yl | p-OCOOC$_2$H$_5$ | H | H | H | 88.3 |
| 13 | 4-OH-quinoline-3-yl | m-OH | H | H | Na | 85.5 |

Table 1-continued

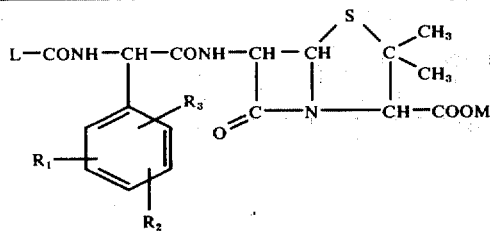

| Example No. | L | $R_1$ | $R_2$ | $R_3$ | M | Purity (%) |
|---|---|---|---|---|---|---|
| 14 | 4-hydroxyquinolin-3-yl | p-OH | m-Cl | H | K | 84.9 |
| 15 | 4-hydroxy-7-methyl-1,8-naphthyridin-3-yl (with CH₃ on pyridine) | p-OCOOC$_2$H$_5$ | H | H | H | 88.1 |
| 16 | 4-hydroxy-1,5-naphthyridin-3-yl | m-OH | H | H | H (triethylamine salt) | 89.0 |
| 17 | 4-hydroxy-7-methylthio-1,8-naphthyridin-3-yl (CH$_3$S-) | p-OCOOC$_2$H$_5$ | H | H | H | 89.5 |
| 18 | 4-hydroxy-7-methyl-1,8-naphthyridin-3-yl (CH$_3$-) | p-OH | H | H | K | 88.0 |
| 19 | 4-hydroxy-7-methoxy-1,8-naphthyridin-3-yl (CH$_3$O-) | p-OH | H | H | K | 85.4 |
| 20 | 4-hydroxy-7-nitroquinolin-3-yl (NO$_2$-) | p-OCOOC$_2$H$_5$ | H | H | H | 81.5 |
| 21 | C$_6$H$_5$CH$_2$OOCNH— 4-hydroxyquinolin-3-yl | p-OH | H | H | K | 84.2 |
| 22 | 6-hydroxy-4-hydroxy-1,5-naphthyridin-3-yl (HO-) | p-OH | H | H | K | 78.1 |

Table 1-continued

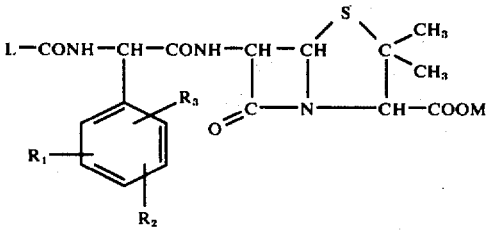

| Example No. | L | $R_1$ | $R_2$ | $R_3$ | M | Purity (%) |
|---|---|---|---|---|---|---|
| 23 | CH₃CONH-substituted naphthyridine-OH | p-OCOOC₂H₅ | H | H | H | 83.0 |
| 24 | H₂N-substituted naphthyridine-OH | p-OH | H | H | K | 85.7 |
| 25 | (CH₃)₂N-substituted naphthyridine-OH | p-OCOOC₂H₅ | m-Cl | H | H | 89.4 |
| 26 | naphthyridine-OH | m-OH | H | H | K | 87.0 |
| 27 | quinoline-2-OH | p-OH | H | H | H | 80.0 |
| 28 | OCH₃, CH₃O-substituted pyrimido-pyridine-OH | p-OH | H | H | Na | 83.2 |
| 29 | naphthyridine-OH | p-OH | H | H | K | 87.5 |
| 30 | (CH₃)₂N-substituted pyrimido-pyridine-OH | p-OCOO—CH₂CH(CH₃)₂ | H | H | H | 77.3 |
| 31 | CH₃-substituted pyrimido-pyridine-OH | p-OH | H | H | K | 81.0 |

Table 1-continued

Structure:
L—CONH—CH—CONH—CH—CH—S—C(CH₃)₂
           |              |    |
           Ar(R₁,R₂,R₃)   C=O—N—CH—COOM

| Example No. | L | R₁ | R₂ | R₃ | M | Purity (%) |
|---|---|---|---|---|---|---|
| 32 | 8-hydroxy-1,5-naphthyridin-2-yl (OH) | p-OH | m-Cl | H | K | 87.8 |
| 33 | 7-hydroxy-1H-pyrazolo[3,4-b]pyridin-5-yl (OH) | p-OCOOC₂H₅ | H | H | H | 88.0 |
| 34 | 4-hydroxypyrido[3,4-d]pyrimidin-7-yl (OH) | p-OH | H | H | K | 87.3 |
| 35 | 2,4-dimethyl-substituted hydroxypyridopyrimidinyl (OH, CH₃, CH₃) | p-OH | H | H | K | 82.1 |
| 36 | 2,4-dimethoxy hydroxypyridopyrimidinyl (OH, OCH₃, OCH₃) | p-OCOOC₂H₅ | H | H | H | 80.1 |
| 37 | 1,5-naphthyridinyl-OCOOC₂H₅ | p-OCOOC₂H₅ | H | H | H | 90.2 |
| 38 | 6,7-methylenedioxy-4-mercaptoquinolin-3-yl (SH) | p-OCOOC₂H₅ | H | H | H | 75.9 |
| 39 | 4-mercapto-1,5-naphthyridin-3-yl (SH) | p-OCOOC₂H₅ | H | H | H | 88.1 |
| 40 | 4-mercaptopyrido[2,3-d]pyridazinyl (SH) | p-OH | m-Cl | m'-Cl | K | 77.3 |

Table 1-continued

[Structure: L—CONH—CH—CONH—CH—CH (with S, C(CH3)(CH3), CH—COOM ring); phenyl with R1, R2, R3]

| Example No. | L | R₁ | R₂ | R₃ | M | Purity (%) |
|---|---|---|---|---|---|---|
| 41 | [4-hydroxy-pyrido-pyrazine with CH₃O-CH=N- substituent] | p-OH | H | H | H | 82.5 |
| 42 | [4-hydroxy-thieno-pyridine] | p-OCOOC₂H₅ | H | H | H | 85.1 |
| 43 | [4-mercapto-1,5-naphthyridine, SH] | p-OH | H | H | K | 88.3 |

Note:
1) The penicillins (I) in Example Nos. 16, 26 and 40 are in the DL-configuration, and the others are all in the D-configuration.
2) The purity was determined by iodometry.

EXAMPLE 44

Preparation of D-α-(4-hydroxy-1,5-naphthyridine-3-carboxamido)-p-hydroxybenzylpenicillin:

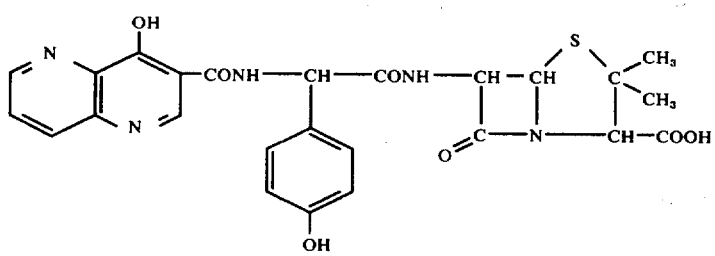

To a mixture of 3.9 g of D-α-amino-p-hydroxybenzylpenicillin, 40 ml of dimethylformamide and 1.88 g of triethylamine, 2.8 g of the N-hydroxysuccinimide ester of 4-hydroxy-1,5-naphthyridine-3-carboxylic acid and 20 ml of dimethylformamide were added, and stirring was effected at room temperature for 5 hours. The resulting mixture was poured into 160 ml of acetone and stirred for 20 minutes. Then, the reaction mixture was filtered, and the collected substance was washed with acetone and dichloromethane in order and dried at 30 to 40° C under reduced pressure to give 4.9 g of D-α-(4-hydroxy-1,5-naphthyridine-3-carboxamido)-(-)p-hydroxybenzylpenicillin triethylamine salt. A mixture of 4.3 g of the thus prepared triethylamine salt, 30 ml of dimethylformamide and 1.34 g of sodium 2-ethylhexanoate was dropwise added to 150 ml of acetone. The precipitate crystals were collected by filtration, washed with acetone and dried under reduced pressure to give 3.5 g of D-α-(4-hydroxy-1,5-naphthyridine-3-carboxamido-p-hydroxybenzylpenicillin sodium salt Purity (determined by iodometry), 910000040039133 %.

N-Hydroxysuccinimide ester of 4-hydroxy-1,5-naphthyridine-3-carboxylic acid used as the starting material in the above Example was prepared as follows:

To a mixture of 7.6 g of 4-hydroxy-1,5-naphthyridine-3-carboxylic acid, 5.06 g of N-hydroxypuccinimide and 150 ml of dimethylformamide, there were dropwise added 5.72 g of thionyl chloride, and the resulting mixture was stirred at room temperature for 16 hours. Then, 8.23 g of pyridine were dropwise added thereto at a temperature below 10° C, and stirring was continued at room temperature for 4 hours. The precipitate was collected by filtration, washed with dimethylformamide and acetone in order and dried to give 11.2 g of N-hydroxysuccinimide ester of the 4-hydroxy-1,5-naphthyridine-3-carboxylic acid. M.P. 258 to 260° C (decomp.).

When determined according to the agar dilution method, the penicillins (I) afford the minimal inhibitory concentrations against test microorganisms as shown in Table 2.

Table 2

| Example No. | Minimal inhibitory concentration (µg/ml) | | | | | |
|---|---|---|---|---|---|---|
| | Staphylo- coccus aureus 209P | Escheri- chia coli NIHJ | lla Proteus miravilis GN2425 | monas Proteus vulgaris HV19 | Klebsie- pneumo- niae PC1602 | Pseudo- aerugi- nosa 104 |
| 1 | 0.78 | 1.56 | 1.56 | 0.025 | 12.5 | 1.56 |
| 2 | 1.56 | 3.13 | 3.13 | 0.025 | 25 | 1.56 |
| 3 | 1.56 | 1.56 | 1.56 | 0.1 | 3.13 | 3.13 |
| 4 | 0.39 | 6.25 | 6.25 | 0.2 | 12.5 | 6.25 |
| 5 | 1.56 | 3.13 | 3.13 | 0.05 | 12.5 | 3.13 |
| 6 | 0.78 | 6.25 | 6.25 | 0.2 | 25 | 6.25 |
| 7 | 0.78 | 1.56 | 3.13 | 0.05 | 12.5 | 1.56 |
| 8 | 0.78 | 12.5 | 12.5 | 0.78 | 25 | 12.5 |
| 9 | 1.56 | 3.13 | 3.13 | 0.05 | 12.5 | 3.13 |
| 10 | 0.39 | 3.13 | 0.78 | — | 3.13 | 3.13 |
| 11 | 0.78 | 12.5 | 3.13 | — | 0.78 | 12.5 |
| 12 | 0.78 | 3.13 | 3.13 | 0.2 | 25 | 6.25 |
| 13 | 0.78 | 6.25 | 3.13 | 0.2 | 25 | 6.25 |
| 14 | 0.78 | 6.25 | 6.25 | — | 25 | 6.25 |
| 15 | 1.56 | 3.13 | 6.25 | 0.1 | 12.5 | 3.13 |
| 16 | 1.56 | 3.13 | 3.13 | 0.05 | 25 | 3.13 |
| 17 | 0.78 | 1.56 | 1.56 | 0.1 | 3.13 | 1.56 |
| 18 | 0.78 | 1.56 | 1.56 | 0.05 | 12.5 | 1.56 |
| 19 | 0.78 | 3.13 | 3.13 | 0.05 | 12.5 | 3.13 |
| 20 | 0.78 | 12.5 | 6.5 | — | 3.13 | 12.5 |
| 21 | 0.39 | 12.5 | 12.5 | — | 3.13 | 12.5 |
| 22 | 0.78 | 1.56 | 1.56 | 0.05 | 12.5 | 3.13 |
| 23 | 1.56 | 3.13 | 3.13 | 0.2 | 25 | 3.13 |
| 24 | 1.56 | 1.56 | 3.13 | 0.05 | 12.5 | 3.13 |
| 25 | 0.78 | 3.13 | 3.13 | 0.05 | 12.5 | 3.13 |
| 26 | 1.56 | 3.13 | 3.13 | 0.05 | 25 | 3.13 |
| 27 | 0.78 | 6.25 | 3.13 | 0.2 | 12.5 | 6.25 |
| 28 | 0.78 | 3.13 | 3.13 | 0.05 | 12.5 | 3.13 |
| 29 | 0.78 | 12.5 | 12.5 | 0.2 | 25 | 6.25 |
| 30 | 0.78 | 6.25 | 3.13 | 0.05 | 12.5 | 6.25 |
| 31 | 0.78 | 3.13 | 3.13 | 0.1 | 12.5 | 3.13 |
| 32 | 0.78 | 3.13 | 6.25 | 0.05 | 25 | 3.13 |
| 33 | 0.78 | 3.13 | 3.13 | 0.1 | 12.5 | 6.25 |
| 34 | 0.78 | 1.56 | 1.56 | 0.05 | 12.5 | 1.56 |
| 35 | 0.78 | 1.56 | 1.56 | 0.025 | 12.5 | 1.56 |
| 36 | 0.78 | 3.13 | 3.13 | 0.05 | 25 | 3.13 |
| 37 | 0.78 | 1.56 | 1.56 | 0.025 | 12.5 | 1.56 |
| 38 | 0.39 | 6.25 | 3.13 | 0.2 | 6.25 | 3.13 |
| 39 | 0.78 | 1.56 | 1.56 | 0.05 | 6.25 | 1.56 |
| 40 | 1.56 | 12.5 | 6.25 | 0.2 | 25 | 6.25 |
| 41 | 1.56 | 6.25 | 6.25 | 0.2 | 25 | 3.13 |
| 42 | 0.78 | 3.13 | 6.25 | 0.2 | 12.5 | 6.25 |
| 43 | 0.78 | 1.56 | 1.56 | 0.025 | 6.25 | 1.56 |
| Compound R | 0.78 | 100 | 50 | 0.39 | 50 | 50 |
| Ampi- cillin | 0.1 | 6.26 | 1.56 | 1.56 | 50 | > 200 |
| Amoxy- cillin | 0.2 | 12.5 | 3.13 | 12.5 | > 200 | > 200 |
| Car- beni- cillin | 0.78 | 12.5 | 0.78 | 0.78 | > 200 | 50–100 |

Note: The compound R is described in U.S. Pat. No. 3,433,784 and has the following chemical structure:

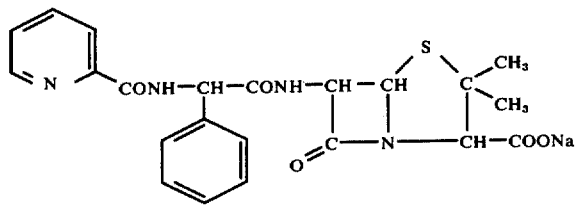

What is claimed is:
1. A compound of the formula:

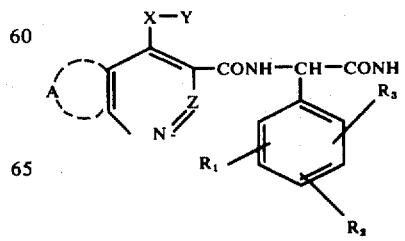

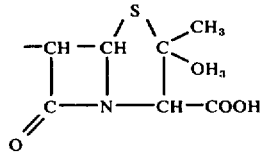

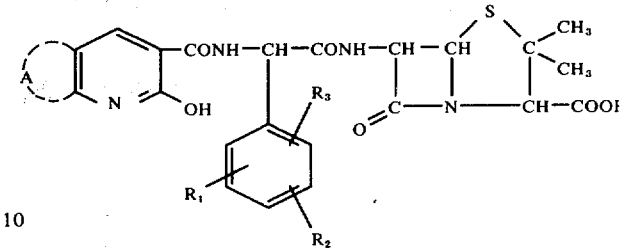

wherein Z is a nitrogen atom or a methylene group, the ring A is a benzene, pyrazole, thiazole, imidazole, pyrazine, pyridazine or pyrimidine ring when Z is a nitrogen atom or a methylene group, or a pyridine ring when Z is a nitrogen atom, the ring A being unsubstituted on being substituted with one on more substituents selected from the group consisting of lower alkyl, lower alkoxy, lower alkylthio, lower haloalkyl, lower alkylenedioxy, halogen, hydroxyl, nitro, amino, lower alkoxycarbonylamino, lower alkylamino, di(lower)alkylamino and lower alkanoylamino, $R_1$ is hydroxyl, lower alkanoxyloxy, lower alkoxycarbonyloxy or benzyloxycarbonyloxy, $R_2$ and $R_3$ are each hydrogen or halogen, X is oxygen or sulfur and Y is hydrogen, lower alkoxycarbonyl or lower alkanoyl, the Y-X- group being present on the carbon atom adjacent to the carbon atom to which the 6-(α-aminoacylamido)penicillanic acid moiety is linked, and non-toxic pharmaceutically acceptable salts thereof.

2. The compound according to claim 1, wherein Y is a hydrogen atom.

3. The compound according to claim 1, wherein $R_1$ is a hydroxyl group, a $C_1$–$c_6$ alkoxycarbonyloxy group or a benzyloxycarbonyl group and $R_2$ and $R_3$ are each a hydrogen atom or a chlorine atom.

4. The compound according to claim 1, wherein the ring A is an unsubstituted benzene ring or a benzene ring having one or more substituents selected from the group consisting of chlorine, trifluoromethyl, nitro, benzyloxycarbonyl amino and methylenedioxy.

5. The compound according to claim 4, wherein $R_1$ is a hydroxyl group or an ethoxycarbonyloxy group and $R_2$ and $R_3$ are each a hydrogen atom or a chlorine atom.

6. A compound of the formula:

wherein the ring A is a benzene, pyrazole, thiazole, imidazole, pyrazine, pyridazine or pyrimidine ring, said ring being unsubstituted or substituted with one or more substituents selected from the group consisting of $C_1$–$c_8$ alkyl, $C_1$–$c_8$ alkoxy, $C_1$–$c_8$ alkylthio, $C_1$–$c_8$ haloalkyl, $C_1$–$c_3$ alkylenedioxy, halogen, nitro, free or protected amino, $C_1$–$c_8$ alkylamino, di($C_1$–$c_8$)alkylamino and $C_1$–$c_9$ alkanoylamino, $R_1$ is a free or protected hydroxyl group and $R_2$ and $R_3$ are each a hydrogen atom or a halogen atom, and non-toxic, pharmaceutically acceptable salts thereof.

7. A compound of the formula:

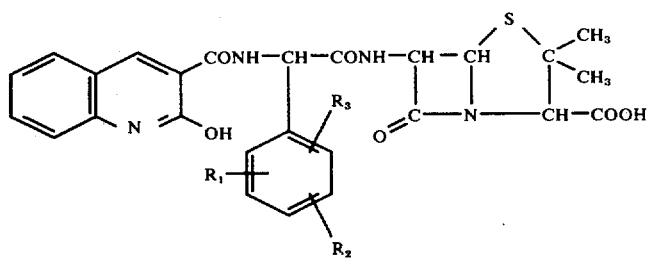

wherein $R_1$ is a free or protected hydroxyl group and $R_2$ and $R_3$ are each a hydrogen atom or a halogen atom.

8. A compound of the formula:

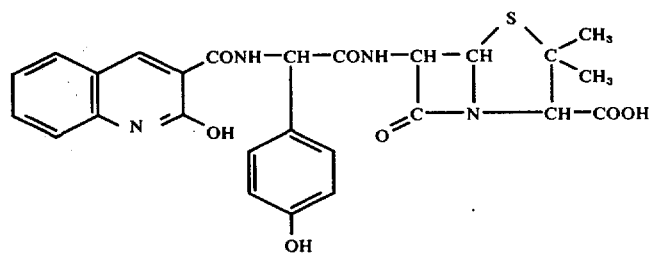

9. D-α-(7-Chloro-4-hydroxyquinoline-3-carboxamido)-p-ethoxycarbonyloxybenzylpenicillin and non-toxic, pharmaceutically acceptable salts thereof.

10. D-α-(4-Ethoxycarbonyloxyquinoline-3-carboxamido)-p-ethoxycarboxyloxybenzylpenicillin and non-toxic, pharmaceutically acceptable salts thereof.

11. D-α-(4-Hydroxyquinoline-3-carboxamido)-m-chloro-p-hydroxybenzylpenicillin and non-toxic, pharmaceutically acceptable salts thereof.

12. D-α- 8-Hydroxypyrido[3,2-d]pyrimidine-7-carboxamido -p-hydroxybenzylpenicillin and non-toxic, pharmaceutically acceptable salts thereof.

13. D-α- 2,4-Dimethyl-8-hydroxypyrido[3,2-d]-pyrimidine-7-carboxamido -p-hydroxybenzylpenicillin and non-toxic, pharmaceutically acceptable salts thereof.

* * * * *